United States Patent [19]

Napier

[11] 4,011,136

[45] Mar. 8, 1977

[54] BIOCHEMICAL PROCESS

[75] Inventor: Eunice Jean Napier, Mattingley, England

[73] Assignee: Glaxo Laboratories Limited, Greenford, England

[22] Filed: July 22, 1974

[21] Appl. No.: 490,844

[30] Foreign Application Priority Data

July 23, 1973 United Kingdom ............ 35057/73

[52] U.S. Cl. .............................. 195/31 R; 195/62; 195/66 R
[51] Int. Cl.$^2$ .................... C07G 7/02; C07G 7/028
[58] Field of Search ............ 195/65, 66 R, 62, 31 R

[56] References Cited

UNITED STATES PATENTS 3,804,718  4/1974  Okada et al. .................... 195/66 R Primary Examiner—A. Louis Monacell
Assistant Examiner—Esther L. Massung
Attorney, Agent, or Firm—Bacon & Thomas

[57] ABSTRACT

A bacterial B-amylase from strains of Bacillus circulans producing no α-amylase can be isolated by simple fractionation techniques and used in the production of maltose, especially high maltose syrups. The enzyme is not inhibited by organomercurials.

13 Claims, No Drawings

BIOCHEMICAL PROCESS

This invention concerns a novel β-amylase and a process for its preparation.

β-Amylases attack the α-1:4 links of the non-reducing ends of the glucose chains in starch to split off maltose units with inversion to the β-form. They are generally found in higher plants, the most widely known and used being barley β-amylase. A bacterial amylase from a *Bacillus polymyxa* has been described but is reported as exhibiting characteristics of both the α- and β- type amylases, thus tending to produce a significant proportion of glucose. This enzyme, like barley β-amylase, has a relatively low temperature for optimal activity.

A bacterial β-amylase from strains of *Bacillus megaterium* has also been described. This seems to have no α-amylase activity and is active at higher temperatures. Both these described enzymes, and that from barley, are inhibited by p-chloromercuribenzoic acid, thus indicating that the active site of the enzymes involves an SH group.

We have now developed a new bacterial β-amylase, derived from *Bacillus circulans*, which is active at higher temperatures than the above known enzyme derived from *B. polymyxa* and which can be prepared containing no α-amylase activity. Because of its bacterial source, this enzyme can be produced on a large scale at relatively low cost compared with that of β-amylase of higher plant origin. The enzyme is, most importantly, not inhibited by organomercurials such as p-chloromercuribenzoates and p-chloromercuriphenyl sulphonates thus indicating that the active site does not involve a SH group. This has the advantage that activity is not dependent on the absence of sulphydryl inhibitors, such as heavy metals. All previously described β-amylases have been inhibited by organomercurials. The enzyme is of particular use in the degradation of starch to prepare maltose solutions of use in the confectionery, baking and brewing industries.

According to the present invention therefore we provide a β-amylase derived from a strain of *Bacillus circulans*, especially strain NCIB 11,033, or an organism derived therefrom by selection or artificial mutation, having the following characteristics:

a. at 37° C the pH for its optimal activity on glycogen substrate is 6.5 – 7.5
b. the enzyme is stable at 60° C for at least 30 minutes without substrate (pH 6.0, 0.05M tris/maleate buffer);
c. the enzyme is not significantly inhibited by a sulphydryl-inhibitor such as sodium p-chloromercuriphenyl sulphonate at levels up to 2mM;
d. gel filtration on a porous polyacrylamide gel possessing a MW exclusion limit of 100,000 shows a single peak of β-amylase activity corresponding to a molecular weight of 53,000 to 63,000;
e. the isoelectric point determined by thin layer gel electrofocusing is pH 4.6;
f. neither activity nor thermostability is affected by calcium chloride in the range 0.001 to 0.1 M.

It may further be noted that the enzyme appears to show a greater affinity for glycogen than for starch.

According to a further feature of the invention we provide a process for the production of maltose wherein starch in an aqueous medium is treated with the β-amylase according to the invention.

The reaction with this enzyme proceeds optimally at about 60° C, in contrast to most previously described β-amylases. It may, however, be convenient to use a temperature of about 70° C to inhibit retrogradation, thus a reaction temperature of 50° – 70° is preferable. By this process it is possible after evaporation to obtain maltose syrups of up to 44° Be or more containing over 50% of the carbohydrate in the form of maltose. The starch, preferably thinned starch, is desirably present in the aqueous medium at a concentration of 30 to 40%, advantageously about 35%. The enzyme is preferably present at a level of about 1 to 50, advantageously 20–30, i.u. (40°) per kilogram of starch. An international unit (i.u.) of enzyme as used herein is that amount of enzyme that will liberate 1 μ mole of maltose per minute from an excess of soluble starch at pH 5.5 at the temperature (in ° C) indicated.

The new enzyme may be prepared by submerged aerobic culture of a strain of *B. circulans* which produces β-amylase substantially free from any other extracellular enzyme, in particular, strain NCIB 11,033 or an organism derived therefrom by selection or artificial mutation, in a nutrient medium therefor followed by fractionation to yield fractions rich in said β-amylase. Strains of *B. circulans* which produce β-amylase substantially free from α-amylase can readily be selected by the following test: Single colonies of the strain under test are grown on starch/agar and the agar is then flooded with an aqueous iodine solution. A colony producing β-amylase only shows a purple zone against blue background, but if α-amylase is produced a clear zone is seen.

The nutrient medium may be any medium suitable for the growth of *Bacillus* species. It should contain a source of nitrogen and a carbohydrate source preferably including starch or any of its breakdown products down to and including maltose. The nitrogen source may for example be a conventional yeast extract, peptone or a preparation e.g. tryptose, casein hydrolysate or whey powder but is advantageously simple corn steep liquor which not only produces the best yields but is also very economical. In general, *B. circulans*, and in particular strain NBIB 11,033, produces enzyme well on simple nutrient-media and, in view of the lack of danger of sulphydryl poisoning of the enzyme, is therefore particularly suitable for large scale industrial fermentation, in contrast to the previously described β-amylase-producing bacteria. The carbohydrate source preferably includes a starch or a breakdown product as defined above to ensure the production of the β-amylase. All other carbon sources, including sugars such as lactose, glucose and sucrose, support growth of the bacteria but may strongly suppress formation of β-amylase. An acid-neutralising agent is preferably present and is conveniently provided by addition of chalk. A concentration of 2% chalk has been found to be the optimum.

The most useful medium appears to contain corn steep liquor 2%, starch 4% and chalk 2%.

The most suitable temperature for enzyme production is about 35° to 50° C optimally about 45° C while the optimum starting pH for the fermentation is 7 – 8.

It is particularly convenient that the β-amylase appears to be the only extra-cellular enzyme produced. In particular the β-amylase is substantially free from α-amylases. Thus simple fractionation procedures can be used, for example conventional precipitation techniques in contrast to selective destructive techniques, such as lead acetate precipitation and selective thermal denaturation, used in purifying previously described β-amylase preparations. Thus the broth may be freed from undissolved solid matter by filtration or centrifugation and the enzyme may then be precipitated by addition of a water-miscible organic solvent such as a ketone e.g. acetone or methyl ethyl ketone, or a lower alcohol such as ethanol, isopropanol or butanol. In general, 0.5 to 2, e.g. about 1 volume of cold isopropanol will effect satisfactory precipitation. This crude precipitate may then be further purified by dissolving it in water, dialysing the solution, removing any precipitated matter, reprecipitating by salting out with a soluble salt such as ammonium sulphate, redissolving and dialysing and freeze-drying. In a preferred method, however, the precipitate is dispersed in a buffer (e.g. tris-maleate 0.025 M) at pH 5.5 and treated with a cationic detergent such as cetyl trimethylammonium bromide to precipitate unwanted acidic polysaccharides. The supernatant may then be reprecipitated by addition of water miscible solvent (e.g. isopropanol) and if necessary the process repeated before finally isolating the product from aqueous solution, for example, by freeze-drying.

The strain of B. circulans is preferably strain NCIB 11,033 or an organism derived therefrom by selection or artificial mutation. According to a further feature of the present invention therefore we provide a process for the growth of a strain of B. circulans which produces β-amylase substantially free from α-amylase, wherein B. circulans strain NCIB 11,033 or an organism derived therefrom by selection or artificial mutation, is cultured on a nutrient medium therefor.

The advantage of a β-amylase substantially free from α-amylase is that it enables carefully controlled hydrolysis reactions to be effected. Thus for maltose production a purer product is obtained when thinned starch is hydrolysed with β-amylase in the absence of α-amylase. The thinned starch should preferably have a dextrose equivalent of less than 10, e.g. about 5 or even lower.

For producing less pure maltose preparations e.g. high maltose syrups, other enzymes such as α-amylase or isoamylase may also be added in controlled amounts, depending on the amount of breakdown of the amylopectin skeleton required. In particular an α-amylase also having a high optimum temperature such as that described and claimed in British Patent Specification No. 1,285,173 may be added to enable optimal starch hydrolysis to be achieved.

An additional use of pure β-amylase is in producing β-limit dextrin for use in the estimation of α-amylase e.g. in flour.

In general the invention provides a β-amylase of high thermostability and low sensitivity to sulphydryl poisons, and which is substantially free from α-amylase, by an economical industrial process, namely submerged aerobic culture of bacteria, thus making possible a particularly convenient and economical process for the preparation of sugar syrups having a high maltose content.

The following Examples are given by way of illustration (all temperatures are in °C; the words Oxoid, Unicam and Difco are registered Trade Marks).

EXAMPLE 1

Preparation of inoculum

The organism (B. circulans strain NCIB 11,033) is inoculated for slopes of starch agar (1% soluble starch, 0.5% Oxoid Peptone, 0.2% yeast extract, 0.04% $K_2HPO_4$, 0.005% $MgSO_4 7H_2O$, 0.01% NaCl, 0.001% $FeCl_3$, 1% agar) to a seed stage of 2% yeast extract, 2% tryptone and 0.5% starch (30 ml per 250 ml shake flask) and grown for 2–24 hours at 50° C on a shaker.

FERMENTATION

The inoculum (1–2%) was transferred to the fermentation medium (2% corn steep liquor, 4% starch, 2% chalk at pH 7.0) at 30 ml per 250 ml shake flask and grown for 48–72 hours at 50° C on a shaker. A liter of 3.4 i.u. (20°)/ml was obtained.

The broth was centrifuged and precipitated with 10 volumes of acetone. The resulting precipitate was taken up in 1/20 volume of water, dialysed overnight and the insoluble material removed by centrifugation. The enzyme was precipitated from the supernatant by adding ammonium sulphate at 50 grams per 100 ml and the precipitate redissolved in water and dialysed before being freeze-dried.

A similar result was obtained using 4 vols of cold ethanol instead of 10 vols acetone. The enzyme so produced had the following characteristics:

a. at 60° C the pH for its optimal activity is 5.0–6.5;
b. the enzyme is not significantly deactivated by a sulphydryl-inhibitor such as sodium p-chloromercuribenzoate at levels up to $10^{-4}M$;
c. neither activity nor thermostability is affected by calcium chloride in the range 0.001 to 0.1 M;
d. the temperature for optimal activity is about 60° C in a pH range of 5.0 to 6.5, the activity falling off rapidly at 65° C in the absence of substrate;
e. the enzyme is stable at 60° C for at least 30 minutes without substrate (pH 6.0, 0.05m tris-maleate buffer).

EXAMPLE 2

Fermentation

The inoculum was prepared as in Example 1 and used at 24 hours to inoculate (2% v/v) two 5-liter fermenters batched with sterile corn steep liquor (2% wet weight), chalk (2% w/v), soluble starch (4% w/v) medium. After 24 hours growth at 45° C, 550 rev./min and air intake of 3 liters per minute the pH had fallen from about 7.0 to 6.3–6.6 and the turbidity (Unicam SP1300; 1 cm cell; Ilford no. 622 filter) had increased from 2.8–3.4 to 5.6. This inoculum was transferred (2% v/v) to 150 liters sterile fermentation medium in Example 1, and the fermentation continued for 68 hours at 250 rev./min and 3 liters per minute. At this time the pH had risen from 7.4 to 8.3, the turbidity from 4.7 to 5.7, the free reducing sugar was negligible, the total carbohydrate had fallen to ½ its initial level and the β-amylase titer was 6.5 i.u. (35°)/ml.

EXTRACTION

Harvest broth (130 liters) was cooled to 20° and filtered on a rotary vacuum filter with filter-aid precoat. To the filtrate (85 liters) at 4° was added an equal volume of cold isopropanol, and the mixture was allowed to stand (1 hour, 5°) before the precipitate was recovered by centrifugation. The precipitate was dispersed in tris-maleate buffer (0.025M, pH 5.5, 14 liters) and re-adjusted to pH 5.5 with 2N HCl. To the suspension was added 2.4 liters (approximately 0.2 volumes) of a 5% cetrimide (cetyl trimethyl ammonium bromide) solution. After blending, the detergent mix was held at 5° (½ hour) before the precipitate was recovered by centrifugation. The supernatant (14 liters) was cooled to 5° and an equal volume of cold isopropanol was added. After standing (½ hours, 5°), the precipitate was recovered by centrifugation and re-dissolved in 3 liters of tris-maleate buffer (0.025M, pH 5.5), the pH adjusted to 5.5 as before, and re-precipitated at 5° with an equal volume of isopropanol. This procedure was repeated. The final precipitate was recovered by centrifugation and dissolved in 2 liters tris-maleate buffer (0.025M, pH 5.5), before removing residual isopropanol by rotary evaporation at a temperature no higher than 40° C.

The final solution was diluted to 3 liters with distilled water, filtered to clarify, and freeze-dried to yield 524 g final solid. This solid assayed at 483 i.u. (35°)/g.

EXAMPLE 3 B. circulans strain NCIB 11,033 was inoculated into a medium consisting of

| | |
|---|---|
| Corn steep liquor | 20 g/l |
| maize meal | 10 g/l |
| chalk | 20 g/l | at 50 ml per 250 ml flask at pH 6.6. After 4 days on a shaker at 42° a titer of 8.6 i.u. (60°)/ml was obtained in the broth supernatant.

EXAMPLE 4

A fermentation similar to that in Example 3 was effected using as medium

| | |
|---|---|
| Oxoid yeast extract | 20 g/l |
| maltose | 20 g/l |
| chalk | 20 g/l | at pH 7.0 for 3 days at 42° with 30 ml per flask to yield a titer of 5.8 i.u. (60°)/ml.

EXAMPLE 5

In a similar fermentation to that of Example 3 using as medium

| | |
|---|---|
| Difco tryptose | 20 g/l |
| Difco yeast extract | 20 g/l |
| Soluble starch (Hopkin & Williams Analar) | 5 g/l | at pH 7.0 for 3 days at 30 ml per flask, a titer of 3.5 i.u. (60°)/ml was obtained.

EXAMPLE 6

Fermentation

Inoculum was prepared as in Example 1.

5 Fermentations similar to that in Example 1 were effected, 2 using 250 ml shake flasks at 37° (6a and 6e) and 3 using 5 liter stirred fermenters containing 3 liters of medium at 45° and agitated at either 550 r.p.m. and 3 liters/min air (6b and c) or 250 r.p.m. and 6 liters/min air (6d) with a 7.5 cm impeller. At 550 rev./min and an air intake of 3 l.p.m. the maximum titer of 4.0 i.u. (35°)/ml was achieved by harvest at 70 hours, when the pH had risen from 7.0 to 8.75, the free reducing sugar level was low and the total carbohydrate had fallen to one-third of its initial value.

At 250 rev./min and 6 l.p.m. the maximum titer of 3.6 i.u. (35°)/ml was achieved by harvest at 70 hours, when the pH had risen from 7.0 to 7.8, the free reducing sugar was low and the total carbohydrate had fallen to ⅓–½ of its initial value.

Extraction

Whole broth was centrifuged for 30 min., the clear supernatant collected by decanting and the cells discarded. Cold ethanol (A.R.) (0.5 volumes) was slowly added to the cooled supernatant whilst stirring in a bath at 4° and the mixture was then allowed to equilibrate for 60 min. The precipitated enzyme was collected by centrifuation (23,000 g) at 4° and redissolved in 0.025M-tris-maleate buffer, pH 5.5. After removal of the insoluble material by centrifugation (23,000 g) at 4°, the clear supernatant was freeze-dried.

The properties of each solid were compared with those of the product of a fermentation (6f) carried out as described in Example 1.

ACTIVITIES OF β-AMYLASE SOLIDS

| | Activities of β-amylase solids | | | |
|---|---|---|---|---|
| Experiment | Specific Activity i.u. (35°)/mg protein | Potency i.u. (35°)/mg solid | Weight (gm.) | Total Activity i.u. (35°) |
| 6a | 19.5 | 0.82 | 3.4 | 2,805 |
| 6b | 15.0 | 0.45 | 4.6 | 2,070 |
| 6c | 19.5 | 0.60 | 3.8 | 2,280 |
| 6d | 12.2 | 0.60 | 6.8 | 4,080 |
| 6e | 15.8 | 0.38 | 4.4 | 1,650 |
| 6f | 12.5 | 0.62 | 3.3 | 2,063 |

EXAMPLE 7

High Maltose Syrups

Suspensions of 35% acid-hydrolysed starch with approximate Dextrose Equivalent of 16 and containing 7% glucose, 6% maltose and 8.5% maltotriose were incubated with various levels of β-amylase prepared as in Example 1 (using 4 vols of cold ethanol instead of 10 vols. of acetone to precipitate from centrifuged broth) in 25 ml aliquots for 72 hours at 50° C (natural pH, no buffer) and the sugars in the resulting syrup analysed. Three spots only were visible in paper chromatograms: glucose, maltose and maltotriose. No isomaltose was observed. The fermentability of the syrup was checked by incubating a sample with Saccharomyces cerevisiae cells; all the glucose and maltose and most of the maltotriose was consumed.

STARCH DIGEST

| | Starch Digest | | | |
|---|---|---|---|---|
| Enzyme in i.u.(40°)/g starch | Dextrose equivalent of resulting syrup | Sugar (% dry basis) | | |
| | | Glucose | Maltose | Maltotriose |
| 0.0015 | 36.9 | 14.6 | 48.2 | 22.0 |
| 0.0075 | 39.9 | 14.7 | 49.5 | 19.4 |

-continued

| Enzyme in i.u.(40°)/g starch | Starch Digest Dextrose equivalent of resulting syrup | Sugar (% dry basis) | | |
|---|---|---|---|---|
| | | Glucose | Maltose | Maltotriose |
| 0.03 | 42.2 | 11.6 | 58.0 | 17.8 |

The pre-treatment of the starch is obviously of great importance, since enzyme is presumably halted by α-1:6 linkages in the amylopectin molecule.

The maltose was shown to be β-maltose by polarimetry.

EXAMPLE 8:

Purification of crude β-amylase

Purification of 25 g of crude β-amylase (prepared according to Example 2) was carried out by ion exchange chromatography on DEAE cellulose columns. The columns were loaded with 5mM tris/HCl buffer (pH 8.5) containing 1mM dithiothreitol (DTT) and the enzyme eluted with sodium chloride gradients from 0 to 250 mM in the same buffer. The active fractions were dialysed against 5mM 2-mercapto ethanol and freeze-dried. The product contained 31% of the original activity with a specific activity of 16.3 i.u. (37°)/mg dry weight. The material showed, on analysis, 32% by weight carbohydrate and 33% protein and had the following characteristics:

Electrofocusing

Electrofocusing was carried out at 4° C in an 8101 electrofocusing column (LKB Productor) using an Ampholine concentration of 1% and a sucrose gradient. The anode was kept at the bottom of the column and the load applied to the central fractions of the gradient.

Range 3 – 10

Load 20 mg of product from DEAE cellulose column
Running — 450 volts for 65 hours.

Range 3 – 6

Load as above.
Running — 500 volts for 65 hours.

4 ml fractions were collected from the columns and monitored for pH, 280 nm absorbance and β-amylase activity (manual assay against glycogen in phosphate pH7.0). A peak of β-amylase activity was found between pH 4.2 and pH 5. with a maximum at pH 4.6. Thin layer gel electrofocusing showed that at least 90% of the β-amylase activity accurred in a tight band at pH 4.6.

MOLECULAR WEIGHT DETERMINATIONS

Gel filtration was performed on polyacrylamide gel (Biogel P100): using the conditions of Andrews, J. Biochem 95, 569 1965). The molecular weight markers used were:
Crystalline β-amylase from sweet potato: 150,000
Bovine serum albumin faction V: 65–70,000
Ribonuclease from beef pancreas: 13,700

A single peak corresponding to a molecular weight of 58,000 was observed.

pH Optimum

Using the assay method Robyt and Whelan "Starch and its Derivatives" Ed. Radley (Chapman and Hall, London 1968) p.432, a pH optimum of 7.0 on a glycogen substrate at 37° C was found.

Effect of p-chloromercuriphenyl sulphonate

Digests containing glycogen (1mg), β-amylase (2.5mg), phosphate buffer pH 7.0 (40μmoles) and various levels of p-chloromercuriphenyl sulphonate were incubated for 10 minutes at 37° C and β-amylase activity was assayed using the above method of Robyt and Whelan. No significant inhibition was caused by concentrations of up to 2 mM.

EXAMPLE 9

Production of β-limit dextrin a. Three 15 g portions of soluble starch (equivalent to 3 x 13.5 g dry weight) were suspended in 290 ml 50mM tris/maleate buffer (pH 5.5) and heated on a boiling water bath to effect complete solubilization. The solutions were cooled to 60° C and crude β-amylase (prepared by the method of Example 2 (0.159 i.u. (37°)/mg)) added with 10ml of buffer to levels of 1.76, 8.8 and 17.6 i.u. (37°)/g dry starch respectively. The flasks were sealed and incubated at 60° C for 65 hours. Samples were assayed for reducing sugars and were found to correspond to 67, 69 and 69% conversions to maltose respectively. Maltose was the only product detected by paper chromatography. The consistency of the degree of conversion at the three enzyme levels is thought to indicate the production of β-limit dextrin.

b. 2 x 5 ml digests were set up in 50mM sodium phosphate buffer pH 7.0 containing glycogen and amylopectin respectively at a concentration of 2%. β-amylase (Prepared as in Example 8 50mg, 300 i.u. (37°)) was added to each and a few drops of toluene added so that a protective layer was formed at the surface. The solutions were incubated at 37° C (72 hours). The resulting solutions were assayed for maltose production and were found to correspond to conversion efficiencies of 44% (glycogen) and 62% (amylopectin). The solutions were also assayed for glucose using glucose oxidase. No glucose could be detected. The remaining portions of the β-amylase digests were dialysed against 50mM sodium phosphate buffer pH 7.0 (72 hours, 4° C). The dialysed solutions showed no reducing sugar release occurring when treated with further β-amylase, but a marked release of reducing sugars when treated with pancreatic α-amylase. This is taken to indicate that the β-amylase preparation produces a β-limit dextrin on reaction with amylopectin or glycogen and is therefore free of α-amylase Description of B. circulans strain NCIB 11033

1. Morphology

Nutrient broth 24 hours at 37° C

Straight or slightly curved motile rods, single or in chains of 2–5 units, sides parallel, ends rounded. Very few spores formed at this stage. No evidence of capsule.

Leifson's Flagella stain: Flagellae peritrochous.

2. Gram Stain

Nutrient agar 24 hours at 37° C.

Gram negative rods 1.4–3.9 x 0.4–0.75μ, sides parallel, ends rounded. By this time a few organisms had formed spores.

Peptone water 24 hours 37° C. Appearance similar.

Nutrient agar 48 hours 37° C. Gram negative rods, abundant spore formation, spores gram negative, some retaining stain more strongly. Spores ovoid, thick walled 1.2 x 1.9μ average thicker than vegetative cell, frequently with old cell forming sporangial envelope. Spore position variable, central to terminal.

3. Colony Appearance

Nutrient agar 19 hours at 37° C. Colonies 0.5–1mm circular, entire, translucent, opalescent, convex, smooth, shiny. Giant colonies and a few microcolonies showing motility spreading outwards spirally.

Starch agar (Starch 1%, peptone 0.5%, yeast extract 0.2% and mineral salts) 19 hours at 37° C.

Colonies 1–2mm, circular, entire, translucent, opalescent to creamy, convex, smooth, shiny, little or no tendency to spread.

Blood agar. (Nutrient agar + 10% blood) 19 hours at 37° C. Colonies 1–2mm similar to above but flatter and spreading by flowing action over plate. No haemolysis.

Agar Slant

Nutrient agar 3 days at 37° C. Growth scant, spreading translucent sometimes difficult to observe, pale, creamy aggregate at base of slope.

Starch agar (as above) 3 days at 37° C Growth medium, opalescent to creamy, slightly shiny, little or no tendency to flow.

5. Growth in fluid medium

All 24 hours at 37° C

Nutrient broth (static). Turbidity light-medium, no sediment.

Nutrient broth (shaken). Turbidity medium-thick, no sediment.

Peptone water (static). Turbidity light, sediment flocculent, shiny.

Starch broth (static). Turbidity thick, sediment short thread-like.

Starch broth (shaken). Turbidity very thick, creamy, no sediment.

6. Temperature Growth Relationship

| Nutrient agar. | Room temp. | Growth slow-fairly good by 4 days |
|---|---|---|
| | 37° C | Growth good by 24 hours. |
| | 50° C | Very little growth even after 4 days. |
| Starch agar. | 50° C | Good growth after 24 hours |

| 7. Sensitivity of Antimicrobial agents (+ = sensitive, − = not sensitive) | | |
|---|---|---|
| Bacitracin | 5 units | − |
| Chloramphenicol | 10μg | + |
| Sulphafurazole | 100μg | + |
| Neomycin | 10μg | + |
| Nitrofurantoin | 200μg | + |
| Penicillin | 1.5 units | + |
| Streptomycin | 10μg | − |
| Polymyxin B | 10μg | + |
| Erythromycin | 10μg | + |
| Novobiocin | 5μg | + |
| Oleandomycin | 5μg | + |
| Tetracycline | 10μg | + |

8. Biochemical Reactions

Sugar fermentation. 3 days at 37° C — acid, but no gas: glucose, sucrose, maltose, mannitol — strongly acid; lactose, mannose — acid; galactose — weakly acid.
litmus milk not coagulated, turning acid by 24 hours, beige sediment by 6 days.
Gelatin - no liquefaction.
Koser's citrate medium — no growth.
Indole — not produced.
Acetylmethylcarbinol — not produced
Nitrate - reduced to nitrite.
$H_2S$ — produced.
Catalase — positive.
Methylene blue — reduced in 1–1½ hours.
Potato slant — no growth.
Starch — hydrolysed.

I claim:

1. A process for the production of maltose, wherein starch in an aqueous medium is treated with a β-amylase derived from a strain NCIB 11,033 of Bacillus circulans having the following characteristics:
    a. at 37° C the pH for its optimal activity on glycogen substrate is 6.5 to 7.5.
    b. the enzyme is stable at 60° C for at least 30 minutes without substrate (pH 6.0, 0.05M tris/maleate buffer);
    c. the enzyme is not significantly inhibited by the sulphydryl-inhibitor, sodium p-chloromercuriphenylsulphonate at levels up to 2 mM;
    d. gel filtration on a porous polyacrylamide gel possessing a MW exclusion limit of 100,000, shows a single peak of β-amylase activity corresponding to a molecular weight of 53,000 to 63,000;
    e. the isoelectric point determined by thin layer gel electrofocusing is pH 4.6;
    f. neither activity nor thermostability is affected by calcium chloride in the range 0.001 to 0.1 M.

2. A process as claimed in claim 1 wherein the β-amylase is derived from an organism obtained from B. circulans strain NCIB 11,033 by selection or artificial mutation.

3. A process as claimed in claim 1 in which the reaction is effected at a temperature of 50°–70°.

4. A process as claimed in claim 1 in which the starch is present in the aqueous medium at a concentration of 30 to 40%

5. A process as claimed in claim 4 in which the starch is thinned starch.

6. A process as claimed in claim 1 in which the β-amylase is present at a level of 1 to 50 i.u. (40°) per kilogram of starch.

7. A process as claimed in claim 5 in which the β-amylase is present at a level of 20–30 i.u. (40°) per kilogram of starch.

8. The process for the production of β-amylase comprising submerged aerobic culture of a strain of Bacillus circulans producing β-amylase in a nutrient medium therefore followed by fractionation to yield fractions rich in said β-amylase wherein said strain of *B. circulans* is strain NCIB 11,033 and said β-amylase has the following characteristics:

a. at 37° C the pH for its optimal activity on glycogen substrate is 6.5 to 7.5;

b. the enzyme is stable at 60° C for at least 30 minutes without substrate (pH 6.0, 0.05M tris/maleate buffer);

c. the enzyme is not significantly inhibited by the sulphydryl-inhibitor, sodium p-chloromercuriphenylsulphonate at levels up to 2mM;

d. gel filtration on a porous polyacrylamide gel possessing a MW exclusion limit of 100,000, shows a single peak of β-amylase activity corresponding to a molecular weight of 53,000 to 63,000;

e. the isoelectric point determined by thin layer gel electrofocusing is pH 4.6;

f. neither activity nor thermostability is affected by calcium chloride in the range of 0.001 to 0.1 M.

9. A process as claimed in claim 8 in which the nutrient medium contains as a carbohydrate source starch or any of its breakdown products down to and including maltose, and as a nitrogen source corn steep liquor, and an acidneutralising agent.

10. A process as claimed in claim 9 in which the acid neutralising agent is chalk.

11. A process as claimed in claim 9 in which the medium contains corn steep liquor 2%, starch 4% and chalk 2%.

12. A process as claimed in claim 8 in which the temperature of the medium is 35° to 50° at a starting pH of 7-8.

13. A process as claimed in claim 7 in which the strain of *B. circulans* used is an organism derived from NCIB 11,033 by selection or artificial mutation.

* * * * *